(12) United States Patent
Duckett, III (10) Patent No.: US 11,496,693 B2
(45) Date of Patent: Nov. 8, 2022

(54) ENDOSCOPE SYSTEM WITH HIGH DYNAMIC RANGE IMAGE CAPTURE USING IMAGE SENSOR WITH POLARIZATION

(71) Applicant: KARL STORZ Imaging, Inc., Goleta, CA (US)

(72) Inventor: George E. Duckett, III, Castaic, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 100 days.

(21) Appl. No.: 17/173,395

(22) Filed: Feb. 11, 2021

(65) Prior Publication Data

US 2021/0168276 A1    Jun. 3, 2021

Related U.S. Application Data

(63) Continuation of application No. 16/692,292, filed on Nov. 22, 2018, now Pat. No. 10,924,689.

(51) Int. Cl.
| | | |
|---|---|---|
| *H04N 5/235* | (2006.01) | |
| *H04N 5/265* | (2006.01) | |
| *H04N 5/225* | (2006.01) | |
| *G02B 27/28* | (2006.01) | |
| *A61B 1/05* | (2006.01) | |
| *A61B 1/00* | (2006.01) | |
| *G02B 23/24* | (2006.01) | |

(52) U.S. Cl.
CPC ....... *H04N 5/2355* (2013.01); *A61B 1/00009* (2013.01); *A61B 1/05* (2013.01); *G02B 27/281* (2013.01); *G02B 27/283* (2013.01); *H04N 5/2254* (2013.01); *H04N 5/2258* (2013.01); *H04N 5/265* (2013.01); *G02B 23/24* (2013.01); *H04N 2005/2255* (2013.01)

(58) Field of Classification Search
CPC .... H04N 5/2355; H04N 5/265; H04N 5/2258; H04N 5/2254; H04N 2005/2255; A61B 1/05; A61B 1/00009; G02B 27/283; G02B 27/281; G02B 23/24
See application file for complete search history.

(56) References Cited

U.S. PATENT DOCUMENTS

| | | | |
|---|---|---|---|
| 7,864,333 B1 * | 1/2011 | Olczak | G02B 27/286 356/491 |
| 2019/0170586 A1 | 6/2019 | Mitani et al. | |
| 2020/0185436 A1 | 1/2020 | Mitani et al. | |

FOREIGN PATENT DOCUMENTS

| | | |
|---|---|---|
| EP | 3482672 A1 | 5/2019 |
| WO | 2018034209 A1 | 2/2018 |

OTHER PUBLICATIONS

Rick, K., European Search Report, Ap. 20206366.5-1209, Mar. 17, 2021, pp. 1-7, Munich.

* cited by examiner

*Primary Examiner* — Nam D Pham
(74) *Attorney, Agent, or Firm* — David Noel Villalpando (57) ABSTRACT

Scopes such as medical imaging camera head devices and methods are provided using light captured by an endoscope system or other medical scope or borescope. At least one polarizing optical element manipulates the polarization properties of image light. The manipulated image light is focused on an image sensor including polarizers for each pixel. Multiple images are produced based sets of pixels having the same orientation of polarizer. The resulting images are combined with high dynamic range techniques.

20 Claims, 9 Drawing Sheets

ENDOSCOPE SYSTEM WITH HIGH DYNAMIC RANGE IMAGE CAPTURE USING IMAGE SENSOR WITH POLARIZATION

CROSS-REFERENCE TO RELATED APPLICATIONS

This application is a continuation of U.S. patent application Ser. No. 16/692,292, filed Nov. 22, 2019 and entitled "Method and Apparatus to improve High Dynamic Range Image Capture Using Image Sensor with Polarization," which is incorporated herein by reference.

TECHNICAL FIELD OF THE INVENTION

The invention relates generally to the field of medical image capture and more specifically to endoscopic camera designs with improved high dynamic range imaging.

BACKGROUND OF THE INVENTION

Dual image acquisition can be a useful feature in the field of endoscopy. Two video streams of the same scene are captured, but each of the captured image streams has different associated characteristics such as a variation in light spectrum, depth of field, or light intensity. In prior dual image systems, images have generally been collected, split in image space, and then focused onto two independent detectors. Such a configuration allows for more versatility than a single image acquisition system, but is generally more expensive and complex, requiring at least two sensors and associated electronics and mounting assemblies.

Some prior art systems capture multiple images from a single image sensor using processing techniques to generate high dynamic range (HDR) images. The intensity level of image light captured varies when acquiring each of the multiple images, generally in rapid succession. A resultant or composite HDR image is created by mathematically combining the multiple images. Such designs have significant limitations due to lack of flexibility in positioning desired optical elements such as filters, lenses, and other elements in the optical path, and due to the delay time of adjusting the light level and acquiring each of the multiple images needed to create an HDR image for the frame.

What is needed are devices and methods to enable an endoscopic camera to acquire HDR images in a cost effective manner. What is further needed are devices allowing the use of varied existing endoscopes for HDR imaging applications and allowing the detection of the varied characteristics in the HDR images.

SUMMARY OF THE INVENTION

It is an object of the invention to provide improved endoscopic acquisition of multiple images, and to allow the use of varied existing endoscopes for multiple imaging applications. It is another object of the invention to enable a simpler and faster method to acquire images of varying intensity necessary to generate HDR images. It is a further object of the invention to permit image analysis to make use of varying states of polarization from a single captured image for purposes such as glare reduction and polarization studies. Endoscopic camera head devices and methods are provided using light captured by an endoscope system. At least one polarizing optical element manipulates the polarization properties of image light. The resulting image light is passed to an image sensor configured with pixels equipped with differently polarizing filters to produce images of differing intensity from the light content collected at different polarization states. The resulting image or images are processed to produce an image with high dynamic range.

According to a first aspect of the invention, an imaging system is provided including an image sensor, a polarizing optical element, and a processor. The image sensor includes a plurality of pixels arranged as a plurality of subgroups each subgroup containing at least two pixels, at least one pixel in a respective subgroup having an associated polarizer, whereby light detected by at least a first pixel of each subgroup is differently polarized than light detected by a second pixel of a subgroup. The polarizing optical element is distal to the sensor which by its polarizing characteristics is capable of controlling the relative intensity detected by the pixels in each subgroup. The processor adapted to receive image data from the image sensor and generate a high dynamic range (HDR) image therefrom.

In a first implementation of the first aspect, the processor is adapted to receive image data from the image sensor and create a plurality of images, each created from a set of pixels spanning a plurality of subgroups and having the same respective polarizer orientation. The processor is further adapted to combine the plurality of images to generate a high dynamic range (HDR) image.

In some implementations of the first aspect, the polarizing optical element changes the relative intensity detected by the pixels in each subgroup dynamically based on the content, such as the intensity value detected at a selected plurality of pixels, of the received image. In such implementations, the polarizing optical element is a polarizer that rotates, thereby adjusting the relative intensity detected by the various pixels in each subgroup dynamically based on the content of the received image. The polarizing optical element may also be a polarizer followed by a variable retarder, and wherein the retardance of the variable retarder is changed thereby changing the relative intensity detected by the various pixels in each subgroup dynamically based on the content of the received image. These dynamic changes can be a result of calculating at least one statistical property for the plurality of images.

In some implementations of the first aspect, the processor is adapted to calculate at least one statistical property for the plurality of images, and based at least in part on the values of the statistical properties, generate a control signal for the polarizing optical element.

In some implementations of the first aspect, the processor is adapted to, when combining plurality of images to generate a HDR image, select a pixel intensity value for each of the plurality of subgroups based on at least one intensity value from a pixel in the subgroup.

In some implementations of the first aspect, the polarizing optical element comprises beamsplitter, splitting an image beam into a first beam with a first polarization and a second beam with a second polarization, the first beam directed to the image sensor including a plurality of pixels of subgroups, and the second beam directed to a second image sensor. A second polarizing optical element may be included along an optical path between the beamsplitter and the image sensor including a plurality of pixels of subgroups.

According to a second aspect of the invention, a method is provided for producing enhanced images from a scope. The method includes collecting image light at the scope from an illuminated scene and directing the image light along an optical channel. The method manipulates the polarization properties of the image light. The image light is focused on an image sensor. The method polarizes image light passing to individual pixels of the image sensor, the pixels arranged as a plurality of subgroups each containing at least two pixels, at least one pixel in a respective subgroup having a respective polarizer oriented in a fixed direction associated therewith. The method receives image data from the image sensor and combines a plurality of pixel data to generate a high dynamic range (HDR) image.

In some implementations of the second aspect, the combination of pixel data to generate an HDR image includes the combination of a plurality of images, each created from a set of pixels having the same respective polarizer orientation. In some implementations, the relative polarizing optical element changes the intensity detected by the various pixels in each subgroup dynamically based on the content, such as the intensity value detected at a selected plurality of pixels, of the received image. In some implementations the changing of the relative intensity is performed by modifying the angle of a rotating polarizer along an optical path, or alternatively changing of the relative intensity is performed by a polarizer followed by a variable retarder, wherein the retardance of the variable retarder is changed, thereby changing the relative intensity detected by the various pixels in each subgroup. The changes can be made dynamically in response to the content of the received image. These dynamic changes can be a result of calculating at least one statistical property for the plurality of images, and based at least in part on the values of the statistical properties, performing the step of changing the relative intensity.

According to another implementation of the second aspect of the invention, the combining the plurality of images to generate a HDR image includes, for each of the plurality of subgroups, selecting a pixel intensity value based on at least one intensity value from a pixel in the subgroup.

In another implementation of the second aspect of the invention, the directed image light is divided into two beams. In some implementations the directed image beam may be split based on polarization characteristics, such that one resulting beam has different polarization characteristics than the other resulting beam. In some implementations of this aspect of the invention, one of the beams may be received by a second image sensor.

These and other features of the invention will be apparent from the following description of the preferred embodiments, considered along with the accompanying drawings.

BRIEF DESCRIPTION OF THE DRAWINGS

The present invention will become more fully understood from the detailed description given herein and the accompanying drawings which are given by way of illustration only, and thus are not limitative of the present invention, and wherein.

DETAILED DESCRIPTION OF EXAMPLE EMBODIMENTS

As used herein, first elements (e.g., sensors and lenses) that are "optically arranged" in relation to other elements, refers to the first elements' position along a common optical path that includes first and other elements. For example, a lens group optically arranged between an image sensor and an objective, means that the lens group occupies a portion of the optical path that light travels (e.g., from the objective to the image sensor) for capturing images or video. Directions such as upstream and downstream refer to the direction of light travel.

Because digital cameras, image sensors and related circuitry for signal capture and processing are well-known, the present description will be directed in particular to elements forming part of, or cooperating more directly with, a method and apparatus in accordance with the invention. Elements not specifically shown or described herein are selected from those known in the art. Certain aspects of the embodiments to be described are provided in software. Given the system as shown and described according to the invention in the following materials, software not specifically shown, described or suggested herein that is useful for implementation of the invention is conventional and within the ordinary skill in such arts.

Figure 1:
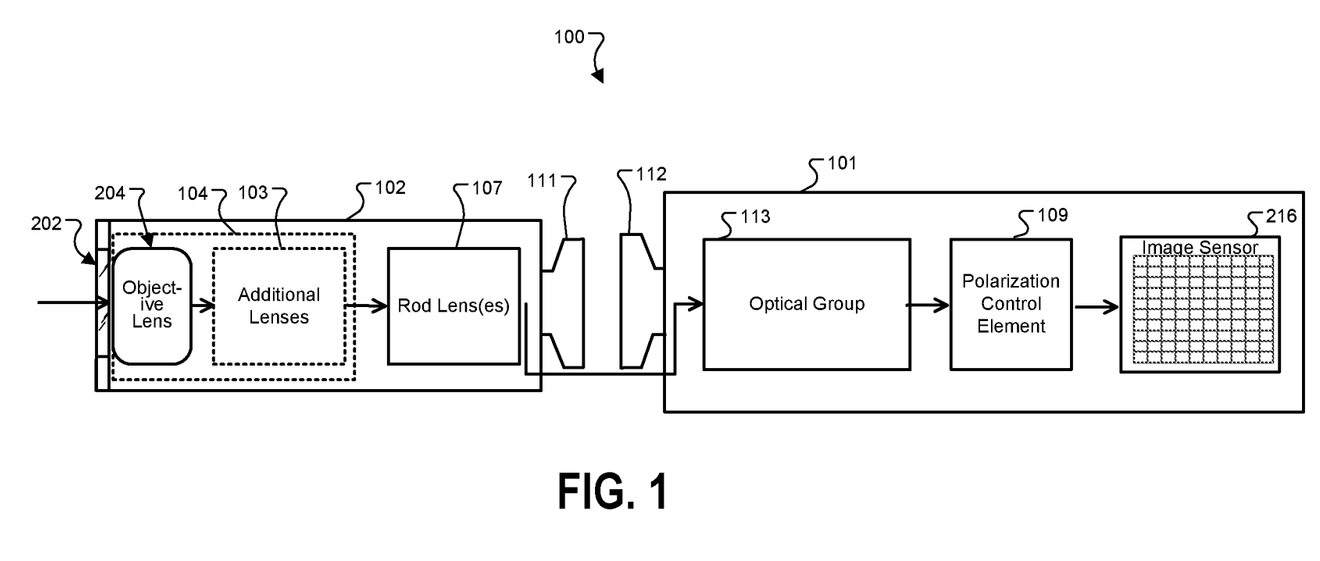
FIG. 1 is a block diagram of a medical imaging device 100 according to an example embodiment of the invention.

FIG. 1 is a block diagram of a medical imaging device 100 according to an example embodiment of the invention. Medical imaging device 100 ("device 100") includes a camera head 101 which may have an endoscope 102 attached via connectors 111 and 112. In some embodiments, an endoscope 102 and camera head 101 may be integrated into a single housing with no connectors needed. In some embodiments, the device 100 is provided as only the camera head 101 adapted to be connected to a suitable endoscope. Connectors 111 and 112 in this embodiment are standard eyecup style optical connectors but may be any suitable connector allowing light to pass from endoscope 102 to camera head 101. Various structural components supporting the depicted elements are omitted in the diagrams herein, as well as other components such as illumination lights sources and controls, which are known in the art and are not shown in order to avoid obscuring the relevant details of the example embodiments of the invention.

Camera head 101 includes an optical group 113 positioned at or behind a central window of connector 112 to receive and condition optical image light from the endoscope 102 which contains one or more focusing lenses for focusing light onto image sensor 216. Optically arranged to receive image light from optical group 113 is a polarization control element 109, which alters the polarization properties of the image light.

The optical group 113 is generally for shaping, directing and focusing light received from the scope 102 onto the image sensor 216. The optical group 113 typically includes at least one focusing lens, with the group having a total positive power. Many suitable lenses and combinations of lenses may be used for optical group 113.

Polarization control element 109 is preferably an adjustable polarization control element which is able to vary the polarization properties of the image light over time. For example, polarization control element 109 may be a rotating polarizer which in operation is rotated to vary polarization direction of the light passed to image sensor 216. Polarization control element 109 may also be constructed with a linear polarizer followed by a variable retarder. In such an embodiment, there is no physical rotation, and polarization is controlled by varying the retardance of the variable retarder. Examples of constructing polarization control element 109 will be further described below.

Image sensor 216 is optically arranged to receive the image light from polarization control element 109. Image sensor 216 includes a plurality of pixels that are arranged as a plurality of subgroups each subgroup containing at least two pixels, at least one of the pixels in a respective subgroup having a respective polarizer. In many implementations each pixel in a respective subgroup has an associated polarizing filter oriented in a different direction from the other polarizing filters associated with the other pixels in the subgroup. In some embodiments one or more pixels of each subgroup may have no associated polarization filter. This arrangement provides ability to differentiate image light of different polarizations, producing multiple images each created from a set of pixels having the same respective polarizer orientation. Because the pixel subgroups of image sensor 216 detect light of different polarizations, polarization control element 109 is capable of controlling the relative intensity detected by the pixels in each subgroup.

Image data from image sensor 216 is generally processed to treat the image data of the multiple images separately, providing images with different intensity ranges. These images are then combined to provide a high dynamic range (HDR) single combined image with higher dynamic range than any of the raw images taken individually. Such processing is described further below.

In some embodiments, system 100 includes an endoscope 102 as depicted at the left of the block diagram. The depicted endoscope is an example only, and many endoscope and borescope designs are suitable, including rigid and flexible endoscopes and borescopes. The exemplar endoscope 102 includes a cover glass 202 at its distal tip, which in this version faces directly along the longitudinal axis of the endoscope 102, but may also be positioned at an angle relative to the longitudinal axis as is known in the art.

Behind, or on the proximal side of, the cover glass 202 is shown a preferred position for the objective lens 204, set against or very near cover glass 202 and preferably assembled together with the cover glass in construction. While a wide-angle lens is preferred for objective lens 204, this is not limiting and any suitable lens may be used in various embodiments. Objective lens 204 may be part of an objective lens group 104 which may include one or more additional lenses 103. The particular number and arrangement of lenses in the endoscope 102 will vary widely depending on the application. Optically arranged or attached at the proximal side of objective lens 204 or objective lens group 104 is a series of one or more rod lenses 107 that serve to pass the light down endoscope 102 towards its proximal end. Typically, several rod lenses 107 are employed, which may be separated by spacers or other lenses in any suitable manner known in the art.

Figure 2:
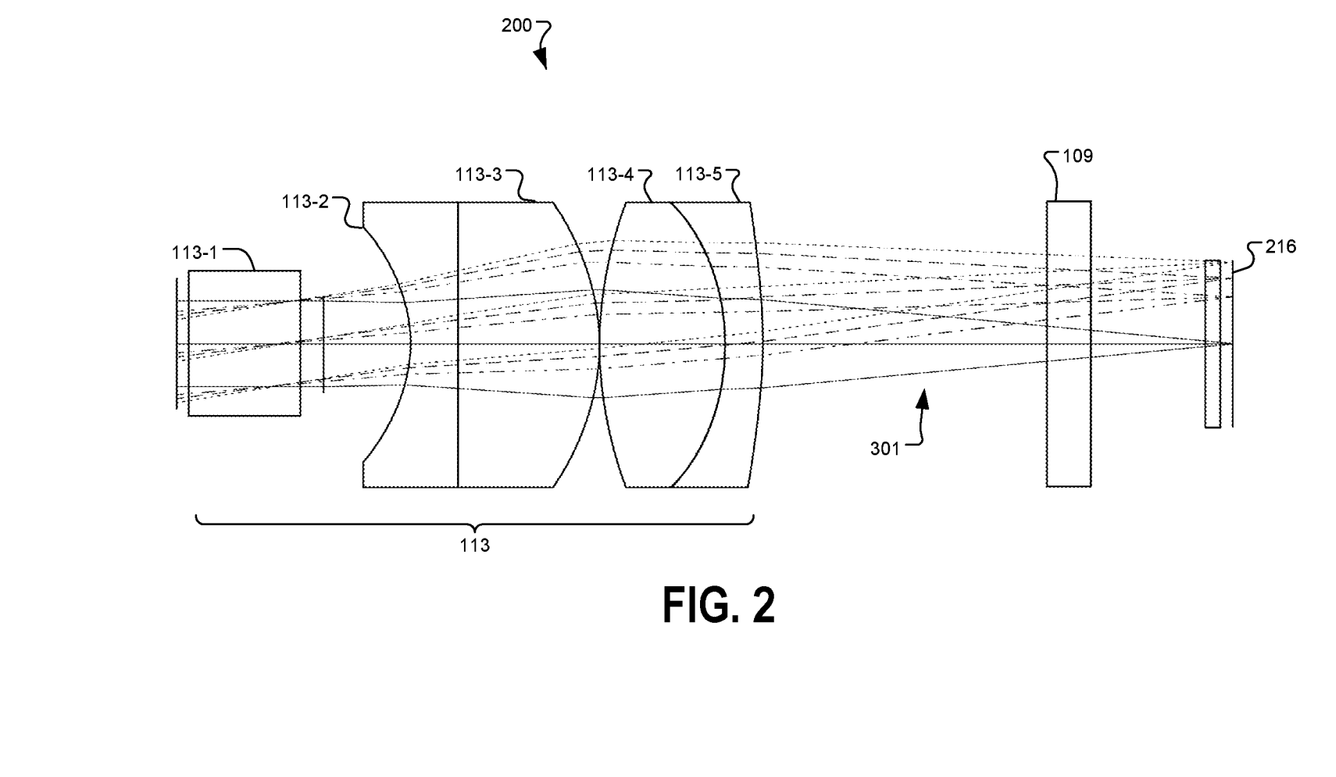
FIG. 2 is a cross section diagram of an optical assembly of a camera head according to some embodiments.

FIG. 2 is a cross section diagram of an optical assembly 200 of camera head 101 of FIG. 1. The view includes a light ray diagram showing the passage of image light through optical assembly 200 to image sensor 216. The depicted optical elements are in diagram form only and are not drawn to scale. Optical assembly 200 includes an optical group 113 which receives light from an attached or integrated endoscope.

The image light received from the scope is directed in the single optical channel of optical group 113. Optical Group 113 includes lenses 113-1, 113-2, 113-3, 113-4, and 113-5. Concave-convex lens 113-1 optically arranged to receive the image light and having a slightly negative optical power spreading the image light to a desired size. Optically arranged to receive image light from lens 113-1 is planoconcave lens 113-2, which has a negative optical power to align the image light. Optically arranged along the planar area of lens 113-2 is convex-plano lenses 113-3, with a positive power for further conditioning the image light, a doublet achromat lens with a biconvex lens 113-4 and a concave-convex lens 113-5. Group 113 has a total positive optical power as indicated by the converging effect on the depicted ray lines.

A polarization control element 109 is optically positioned between optical group 113 and image sensor 216. Polarization control element 109 is arranged to receive the optical image light from optical group 113 and alter the polarization properties of the image light. As discussed above, polarization control element 109 is preferably adjustable and may be constructed in a number of suitable ways, such as described with respect to the examples shown in FIG. 8 and FIG. 11. Polarization control element 109 varies the polarization properties of the incoming light, and this variation may be changed at different time intervals, such that the relative intensity of light at different polarizations is varied as the light is passed to image sensor 216. The light at various polarizations is then detected at image sensor 216 and employed to produce multiple images of different intensities. An HDR image is then produced from the multiple images, with higher apparent dynamic range than either a first or second image taken individually. Further, with multiple images captured containing different polarization characteristics, further advantages may be achieved such as glare reduction and improved feature visibility over a traditional HDR imaging technique. In addition, it is possible to observe polarizing effects of various tissues and other objects under observation.

Figure 3:
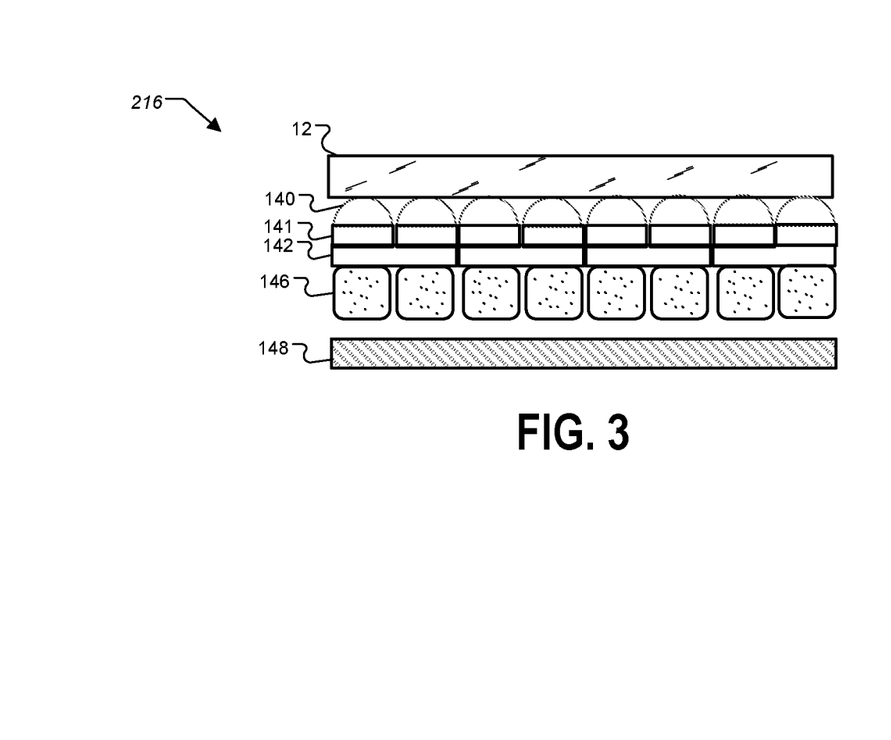
FIG. 3 shows a cross sectional diagram of a portion of a sensor which may be employed in some embodiments.
Figure 4:
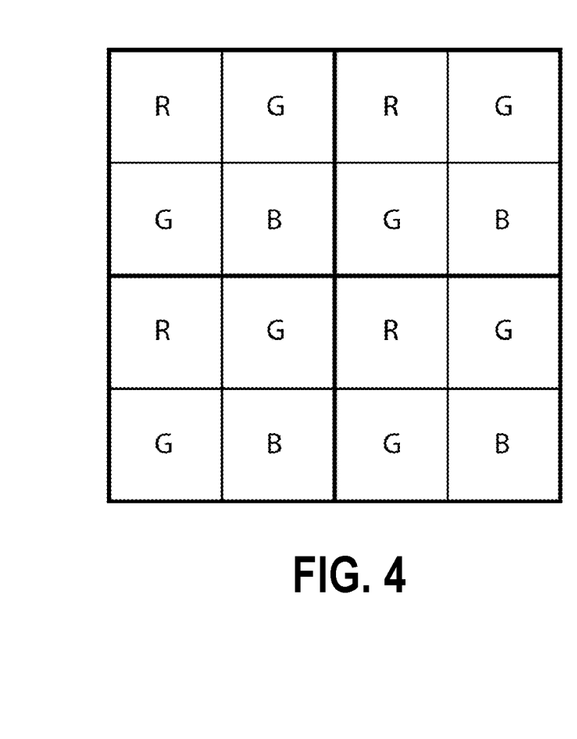
FIG. 4 shows a standard Bayer filter used in most color image capture sensors.
Figure 5:
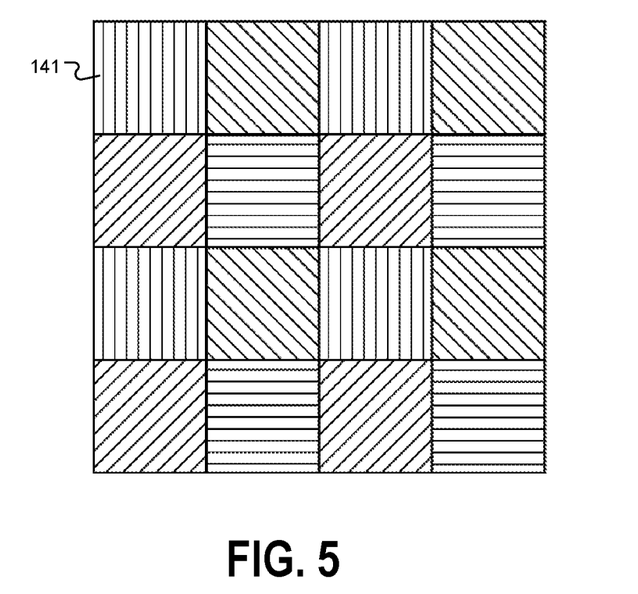
FIG. 5 shows a top diagram view of a segment of an image sensor such as that shown in FIG. 3 wherein each pixel in a group has a different polarizing filter orientation.

FIG. 3 shows a cross sectional diagram of a portion of an example sensor which may be employed in some embodiments. The diagram illustrates the structure of an image sensor chip suitable for use with the techniques disclosed herein, such as the IMX250MYR RGGB image sensor (Sony Semiconductor Solutions Corporation, Japan). In order to more easily illustrate the utility of the polarizing sensor, it may be beneficial to contrast the polarizing sensor with a standard single chip CMOS or CCD sensor employing a Bayer pattern color filter as shown in FIG. 4. A standard Bayer filter image sensor utilizes four individual pixels in a single calculation unit. The image sensor shown in FIG. 4 comprises 16 individual pixels in four separate calculation units. Each of the pixels is covered by an individual color filter. Light energy collected by each individual photodetector located beneath each filter collects a given intensity of light of the color that passes through the filter. Two green pixels have been conventionally used in each calculation unit in order to mimic sensitivity of the human eye to the green part of the visible spectrum, see, for example, U.S. Pat. No. 3,971,065 (Bayer, "Color Imaging Array," issued Jul. 20, 1976), incorporated herein by reference. As a result of the filtering array, each pixel represents only a single color content, and a demosaicing algorithm is generally used to estimate a color and intensity value for each pixel, however it is helpful to remember that the actual collected image resolution is decreased as a result of the Bayer filter in contrast to that a monochromatic image, wherein each pixel represents an actual absolute measured light intensity value. As can be seen in the cross section of the polarizing sensor shown in FIG. 3, according to the image sensors used in the present invention, in contrast to the simple Bayer color filter shown in FIG. 4, pixels are arranged in blocks wherein each pixel in a block is filtered at an individual polarization angle, as illustrated in FIG. 5. The diagram generally shows an idealized cross section of a segment of image sensor 216, showing a small array with very few pixel elements in order to illustrate the construction. However, typically an image sensor will have an array of many hundreds of pixels in each dimension, for example 1028 pixels along one dimension. The sensor construction will vary with different technologies and may include more or less layers, with this example shown for illustration purposes. Sensor 216 includes a cover glass 12, which is typically fixed in packaging or as an element of an integrated sensor assembly. Beneath cover glass 12 are micro-lenses 140 which collect and direct the impinging light toward the photodiodes 146. Each micro-lens 140 is typically associated with a single photodiode. A grid of polarizers 141 is positioned under microlenses 140. FIG. 5 shows a top diagram view of the grid of polarizers 141 for a 4×4 array.

Referring to FIG. 3 and FIG. 5, polarizers 141 are generally constructed with micro-wires in a micro-wire grid frame mounted to a glass substrate which sits above photodiodes 146. Each polarizer includes rows of micro-wires or other structures that only pass light polarized in the direction perpendicular to that of the micro-wires, as is known in the art. Light of other polarizations is increasingly blocked the more the polarization of the incoming light varies from the orientation of the polarizer. As shown in FIG. 5, in this embodiment polarizers 141 are arranged in groups of four, a repeating two-by-two grid, with the lower right depicted polarizer 141 at zero degrees orientation, the lower left at 45 degrees, the upper right at 135 degrees, and the upper left at 90 degrees.

Figure 6:
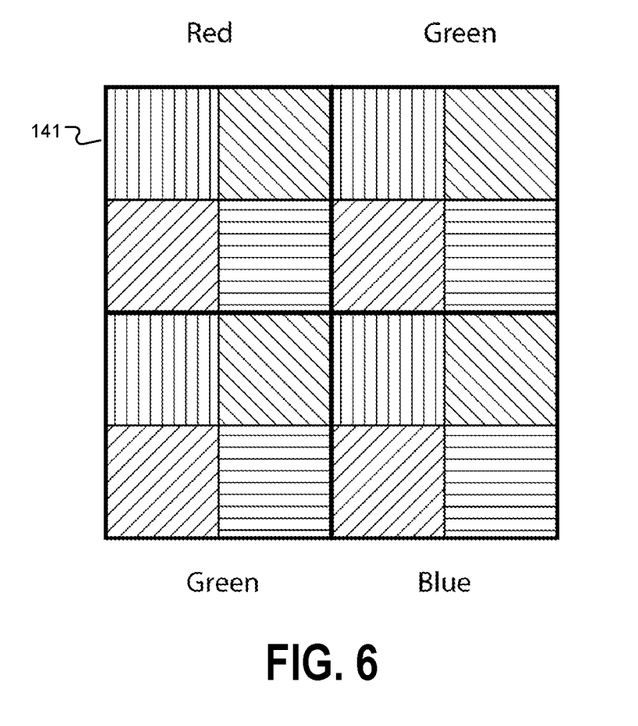
FIG. 6 shows a top down segment of a color (RGB) imaging sensor combining a filter distribution used for the image sensors of FIGS. 4 and 5.

Certain embodiments of this invention make use of a sensor array, a top-view portion of which is illustrated in FIG. 6, wherein polarizers 141 rest atop a color filter layer 142, which includes a color filter array such as a Bayer filter array of red, green, and blue filters discussed above, in which each color filter spans a two-by-two section of polarizers 141 as well as spanning a two-by-two grid of photodiodes 146, illustrating a 4×4 grid, or calculation unit, wherein each polarization state in each color is represented by at least one pixel in the 16 square pixel grid. In this way it can be seen that a trade-off is made between resolution and polarization measurements in an analogous way to the trade-off made when utilizing a Bayer filter on a color sensor. By contrast a color, four-state monochromatic polarization detecting sensor, as shown in FIG. 6, will have approximately half the effective vertical and horizontal resolution of a comparable color sensor, while effectively generating four approximately quarter resolution color images, each detecting light of a unique polarization state. Color filter layer 142 may be integrated with the glass substrate of polarizers 141, or the order may be reversed.

A metalized interconnect layer (not shown) may be between the color filter 142 layer and the photodiode 146 layer, or between the photodiode 146 layer and the carrier substrate 148, and in some cases may be integrated with the photodiode layer. Some sensor designs place the micro-lens 140 layer on-chip, that is, under the color filter 142 layer or under the layer of polarizers 141.

Figure 7:
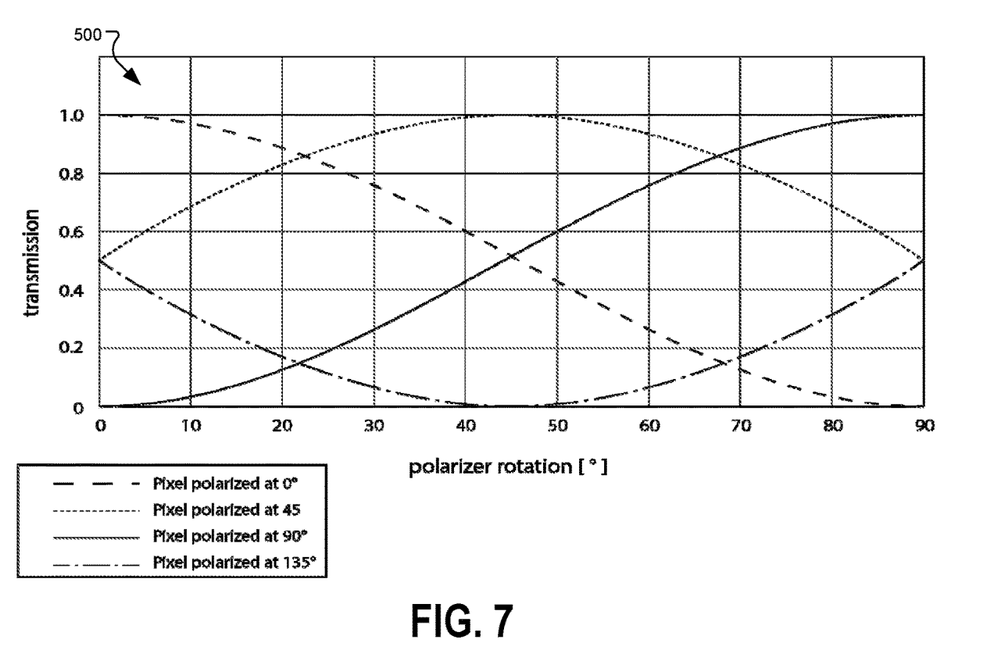
FIG. 7 shows a diagram of the combined transmission of a polarization control element in front of an image sensor with integrated polarizers such as those of FIG. 5.

FIG. 7 shows a diagram of the combined transmission of a polarization control element upstream of an image sensor with integrated polarizers such as those of FIG. 5. The diagram shows four graphs, representing light intensity at four polarization angles of 0 degrees, 90 degrees, 45 degrees, and 135 degrees (the angles passed by the various polarizers in FIG. 5). The diagram shows the effect of a polarization control element with a rotating polarizer, as the polarizer is rotated. The angle of the rotating polarizer is shown along the horizontal axis, and the light intensity of transmitted light is shown on the vertical axis.

As the polarization control element varies the polarization angle of the light, the polarization-sensitive pixels of the image sensor detect light at different intensities. This effect allows the simultaneous capture of multiple images with different intensities for use with HDR imaging. Alternately the captured image data can be otherwise manipulated for various polarization studies or for other purposes.

In non-HDR systems with a single captured image, a feature within the captured image might be washed out or obscured in shadow, depending on the illumination of the scene and the settings of the image sensing apparatus. In traditional HDR systems, an HDR image is constructed from, for example, three images of three different intensity levels including a high intensity (bright) image, a medium intensity image, and a low intensity (dim) image. These images are usually captured in rapid succession while varying the exposure by adjusting the iris, the light source, or the sensor integration time. This allows features to be distinguished even if they are very dim or very bright, by selecting ideally exposed regions of each captured images and combining them, or by using other video processing techniques known in the art. The techniques herein make use of the polarization-sensitive image sensor to capture multiple images of a single scene at various intensity levels determined by the polarization angle of each pixel as well as the state of the polarization control element. In the case of a rotating polarization control element, in the present example, four images can be captured in any of the states of the rotating polarizer. For example, at the fifteen degree rotation position shown on the chart in FIG. 7, the sensor may be used to capture an image from the 0 degree pixels of about 92% of the illumination passing through the rotating polarizer, 75% for the 45 degree pixels, 25% from the 135 degree pixels, and 8% from the 90 degree pixels, providing four images at varying light intensity levels. Or, the sensor may be used to acquire one or more images at a first rotation position and then acquire one or more additional images at another rotation position. In this manner, a precise desired intensity level may be achieved by controlling exactly where on the depicted curves an image is acquired for any particular one of the four sets of polarized pixels.

Figure 8:
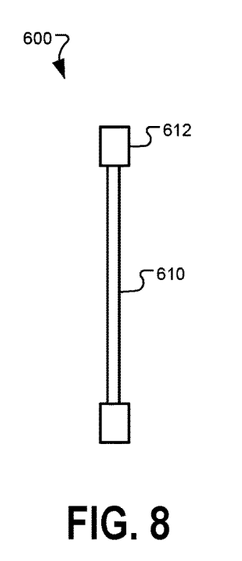
FIG. 8 shows a cross section diagram of a polarization control element constructed as a rotating polarizer according to some embodiments.
Figure 9:
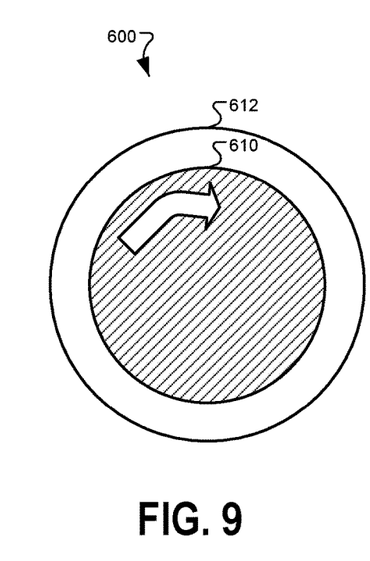
FIG. 9 is a front view diagram of the same polarization control element.

FIG. 8 shows a cross section diagram of a polarization control element 600 constructed as a rotating polarizer according to some embodiments. FIG. 9 is a front view diagram of the same polarization control element 600. The depicted implementation of a polarization control element may be used in the design of FIG. 2, for example, to achieve the effect depicted in FIG. 7. Polarization control element 600 includes a housing 612 forming a circular opening in which a polarizing filter 610 is rotatably mounted. Rotating movement of polarizing filter 610 is depicted by the arrow. Construction of rotating polarizers is known in the art and may include an electric motor or other drive mechanism mounted in housing 612 and operable to produce the rotation using a drive gear matched to grooves along the perimeter of polarizing filter 610. In operation, the drive mechanism may rotate polarizing filter 610 continuously or in discrete movements upon command.

Figure 10:
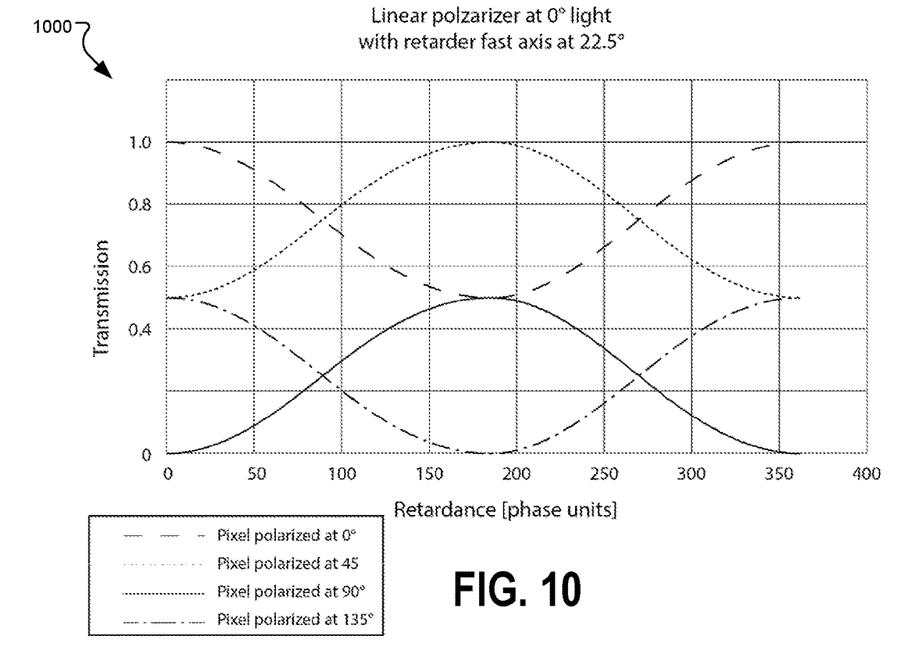
FIG. 10 shows another diagram of the combined transmission of a polarization control element in front of an image sensor with integrated polarizers, using a different polarization control element implementation for this embodiment.

FIG. 10 shows another diagram of the combined transmission of a polarization control element in front of an image sensor with integrated polarizers, using a different polarization control element implementation for this embodiment. Like FIG. 7, the diagram 1000 shows four graphs, representing light intensity at four polarization angles of the sensor's polarizers. The diagram shows the effect of a polarization control element implemented with a variable retarder. The retardance of the variable retarder in phase units (degrees of phase retardance) is shown along the horizontal axis, and the light intensity of transmitted light is shown on the vertical axis.

Similarly to the embodiment of FIG. 7, the polarization-sensitive image sensor may be used to capture multiple images in any of the depicted states of the polarization control element.

Figure 11:
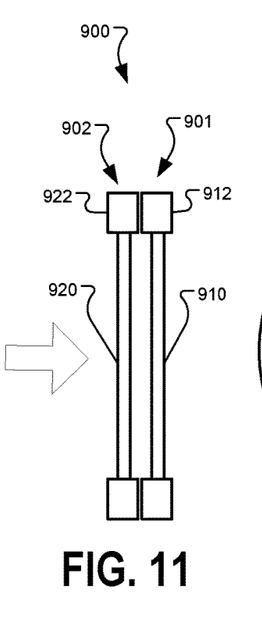
FIG. 11 shows a cross section diagram of a polarization control element including a variable retarder and a linear polarizer according to some embodiments.
Figure 12:
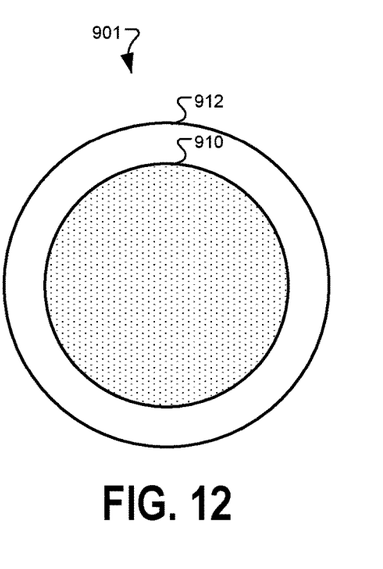
FIG. 12 shows a front view diagram of the variable retarder of FIG. 11.
Figure 13:
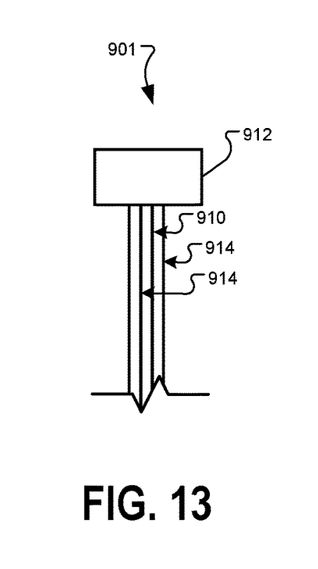
FIG. 13 shows an enlarged cross section view of the variable retarder of FIG. 11.

FIG. 11 shows a cross section diagram of a polarization control element 900 including a variable retarder 901 and a linear polarizer 902 according to some embodiments. FIG. 12 shows a front view diagram of the variable retarder 901 of FIG. 11. FIG. 13 shows an enlarged cross section view of the variable retarder 901 of FIG. 11. Referring to FIGS. 11-13, polarization control element 900 may be used in the embodiment of FIG. 2 or other embodiments in which a polarization control element is optically arranged following a beamsplitter. Polarization control element 900 is depicted with an arrow in FIG. 11 showing the direction of light passage, first through linear polarizer 902 and then through variable retarder 901.

Variable retarder 901 includes a frame 912 with control electronics, and a retarding medium 910. In the cross-section of FIG. 13, the construction of one example retarding medium 910 is shown. Many suitable variable retarder technologies may be used, with a preference for those that can be miniaturized. In this embodiment, retarding medium 910 is a thin layer of a liquid crystal fluid sandwiched between two transparent electrodes 914. The liquid crystal molecules are highly anisotropic. When a voltage is applied to electrodes 914 through electrical circuitry in housing 912, an electric field between electrodes 914 orients the liquid crystal molecules. The field-induced orientation of the liquid crystal molecules causes a change in the index of refraction of the liquid crystal layer. This change results in alteration of the optical phase of light passing through the liquid crystal layer. In operation, variable retarder 901 is controlled to produce at least two different polarization conditions, and typically is varied back and forth across some or all of the depicted range of retardance shown in FIG. 10.

Linear polarizer 902 includes a frame 922 and a linear polarizing filter 920. Many different linear polarizer technologies may be used for linear polarizer 902. The shown fixed orientation of the linear polarizing filter 920 is selected to achieve the result of FIG. 10.

Figure 14:
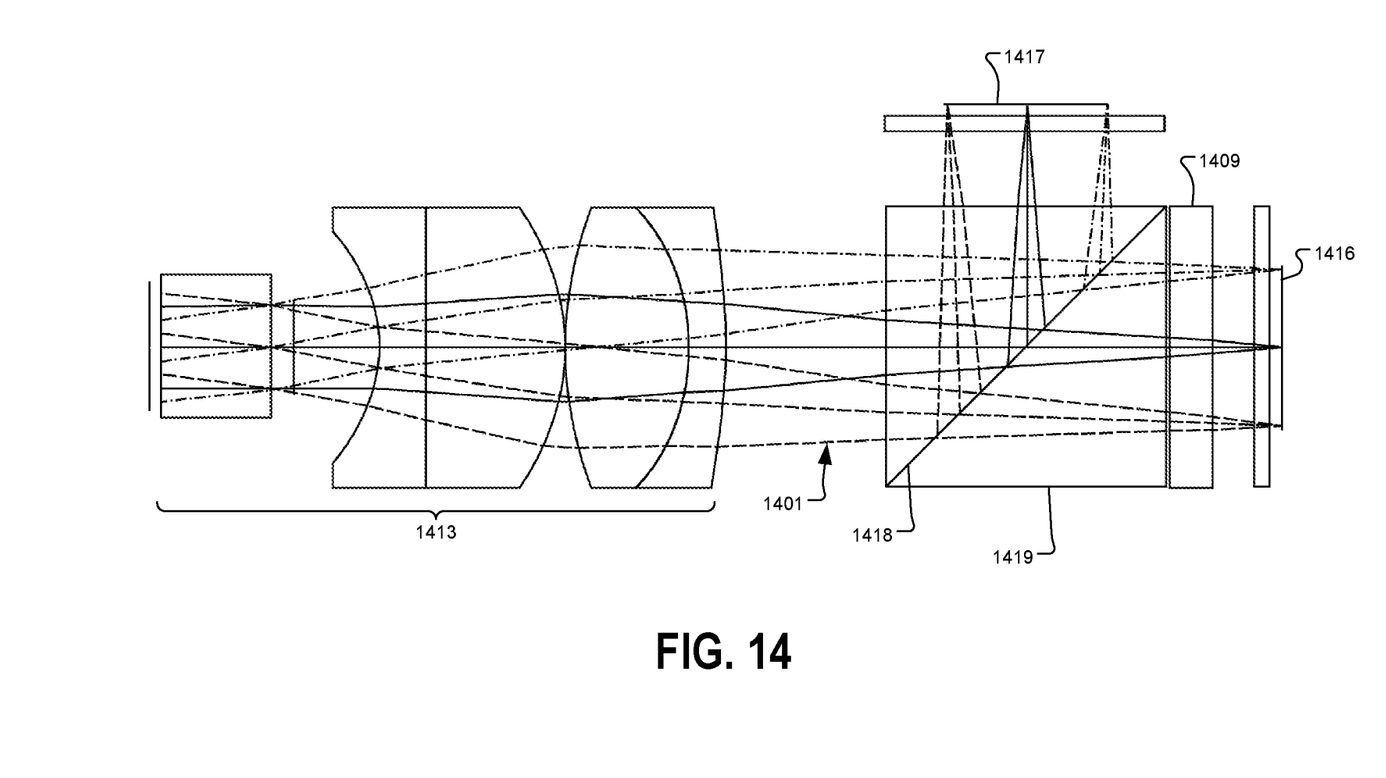
FIG. 14 is a cross sectional view according to some embodiments of the invention where more than one image sensor is used and the incoming beam is split by polarization.

As noted above, certain embodiments of the invention may employ a beamsplitter as part of the optical assembly. In further embodiments, the beam splitter may split the beam based on polarization, as shown in FIG. 14. An optical group 1413 receives light from an attached or integrated endoscope and focuses and directs the image light to image sensors 1416 and 1417. Downstream from the optical group 1413 is a beamsplitter, 1418, which may be part of a beam splitting prism 1419. In a preferred embodiment, the beam splitter may split the incoming light based on polarization, sending light of one polarization towards sensor 1417, while the remaining polarized light beam is directed to a second sensor 1416. The second sensor 1416 in this example is a specialized sensor discussed above, wherein individual pixels are arranged in subgroups, and one or more pixels within those subgroups are equipped with a polarization filter, as shown previously in FIGS. 5 and 6. Between the beamsplitter 1418 and the second sensor 1416 is placed a polarization control element 1409 that may take the form of any of the above mentioned variations or a fixed retarder. In some embodiments, the polarization control element may be absent from the system, the specialized image sensor working in conjunction with the polarizing beam splitter, to provide light of varying intensities directly to the pixels of each subgroup. Light may be split evenly or unevenly. For example, 20% of the light may be directed to the second image sensor 1416, with the remaining light sent to the first image sensor 1417. It should further be noted, that in these embodiments, it may not be necessary, or even desirable, to employ a Bayer filter on the second image sensor 1416. Image data received by the image processor from the second image sensor may then be used to define regions of higher and lower exposure and enhance the dynamic range of a resultant image by combining the data received by the two sensors.

Figure 15:
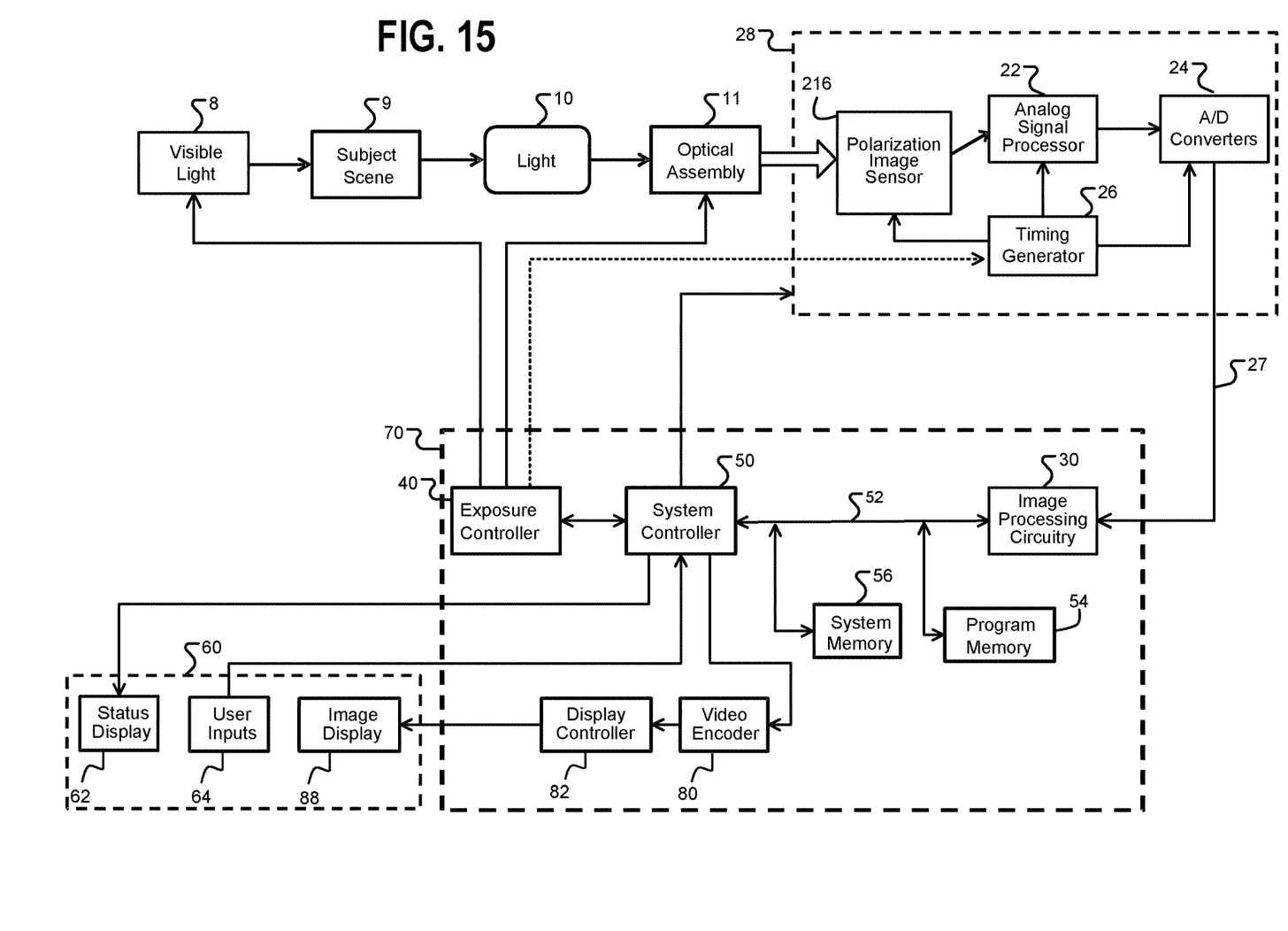
FIG. 15 shows a block diagram of system including an endoscope device and an image capture device according to some embodiments.

FIG. 15 shows a block diagram of system including an endoscope device and an image capture device according to some embodiments. The invention is applicable to more than one type of device enabled for image capture, such as FI-capable endoscopes, other medical or industrial imaging devices. The preferred version is an imaging scope system, such as an endoscope.

The diagram shows a light source 8 which illuminates subject scene 9 with visible light. Fluorescent excitation light may also be used, which may be outside the visible spectrum in the ultra-violet range or the infra-red/near infrared range, or both. Light source 8 may include a single light emitting element configured to provide light throughout the desired spectrum, or a visible light emitting element and a one or more fluorescent excitation light emitting elements. Further, light source 8 may include fiber optics passing through the body of the scope, or other light emitting arrangements such as LEDs or laser diodes positioned at or near the front of the scope.

As shown in the drawing, light 10 reflected from (or, alternatively, as in the case of fluorescence, excitation light 8 absorbed and subsequently emitted by) the subject scene is input to an optical assembly 11, where the light, modified as described herein, passes to image sensor assembly 28 where it is focused to form an image at a solid-state image sensor 216. Optical assembly 11 includes the optics of the endoscope and of the camera head. As discussed above, portions of the optical assembly may be embodied in a camera head attached to a scope, or in a single imaging device. Image sensor 216 converts the incident light to an electrical signal by integrating charge for each picture element (pixel). Image sensor 10 includes polarization sensitive pixels as described herein.

The total amount of light 10 reaching the image sensor 216 is regulated by the light source 8 intensity, the optical assembly 11 aperture, the attenuation of optical path, the polarization filters of the pixels. The exposure can further be controlled by the time for which the image sensor 216 integrates charge. An exposure controller 40 responds to the amount of light available in the scene given the intensity and spatial distribution of digitized signals corresponding to the intensity and spatial distribution of the light focused on image sensor 216. If fluorescence imaging is used, exposure controller 40 also controls the emission of fluorescent excitation light from light source 8, and may control the visible and fluorescent light emitting elements to be on at the same time, or to alternate to allow fluoresced light frames to be captured in the absence of visible light if such is useful in the fluorescent imaging scheme employed. Exposure controller 40 may also control the optical assembly 11 aperture, and indirectly, the time for which the image sensor 216 integrates charge. The control connection from exposure controller 40 to timing generator 26 is shown as a dotted line because the control is typically indirect. Exposure controller 40 may also command the state of polarization control element 109, 1409 in optical assembly 11.

Timing generator 26 produces various clocking signals to select rows and pixels and synchronizes the operation of image sensor 216, analog signal processor 22, and A/D converter 24. Image sensor assembly 28 includes the image sensor 216, the analog signal processor 22, the A/D converter 24, and the timing generator 26. The functional elements of the image sensor assembly 28 can be fabricated as a single integrated circuit as is commonly done with CMOS image sensors or they can be separately-fabricated integrated circuits.

Analog signals from the image sensor 216 are processed by analog signal processor 22 and applied to analog-to-digital (A/D) converter 24 for digitizing the analog sensor signals. The digitized signals each representing streams of images or image representations based on the data, are fed to image processor 30 as image signal 27. The images captured at different polarizations are typically transmitted as separate images within image signal 27.

The system camera control unit (CCU) 70 includes image processing circuitry 30 performing digital image processing functions to process and filter the received images as is known in the art. Image processing circuitry may include separate, parallel pipelines for processing the multiple images separately. CCU 70 may be implemented in a single assembly or may include two or more camera control modules performing different functions such as communication with a specific camera model, and image processing. Such circuitry is known in the art and will not be further described here. Image processing circuitry 30 may provide algorithms, known in the art, for combining two images of the same view but containing different characteristics in a combined image display.

The system controller 50 controls the overall operation of the image capture device based on a software program stored in program memory 54. This memory can also be used to store user setting selections and other data to be preserved when the camera is turned off. System controller 50 controls the sequence of data capture by directing exposure controller 40 to set the light source 8 intensity, the optical assembly 11 aperture, and controlling various filters in optical assembly 11 and timing that may be necessary to obtain image streams. A data bus 52 includes a pathway for address, data, and control signals.

Processed image data are continuously sent to video encoder 80 to produce a video signal. This signal is processed by display controller 82 and presented on image display 88. This display is typically a liquid crystal display backlit with light-emitting diodes (LED LCD), although other types of displays are used as well. The processed image data can also be stored in system memory 56 or other internal or external memory device.

The user interface 60, including all or any combination of image display 88, user inputs 64, and status display 62, is controlled by a combination of software programs executed on system controller 50. User inputs typically include some combination of typing keyboards, computer pointing devices, buttons, rocker switches, joysticks, rotary dials, or touch screens. The system controller 50 manages the graphical user interface (GUI) presented on one or more of the displays (e.g. on image display 88). In particular, the system controller 50 will typically have a mode toggle user input (typically through a button on the endoscope or camera head itself, but possibly through a GUI interface), and in response transmit commands to adjust image processing circuitry 30 based on predetermined setting stored in system memory. Preferably a system employed with any of the device designs herein provides ability to toggle between an individual view of either single image (for example, image 1 or image 2), all individual images, and/or a view of the combined image created with processing of data from all images or image data. Settings may be provided to adjust the manner in which characteristics from the individual images are combined to produce an HDR image, and displayed or stored. Settings may also include different settings for different models of scopes that may be attached to a camera head or other imaging device containing image sensor assembly 28.

Image processing circuitry 30 is one of three programmable logic devices, processors, or controllers in this embodiment, in addition to a system controller 50 and the exposure controller 40. Image processing circuitry 30, controller 50, exposure controller 40, system and program memories 56 and 54, video encoder 80, and display controller 82 may be housed within CCU 70.

CCU 70 may be responsible for powering and controlling light source 8, image sensor assembly 28, and/or optical assembly 11. In some versions, a separate front end camera module may perform some of the image processing functions of image processing circuitry 30.

Although this distribution of imaging device functional control among multiple programmable logic devices, processors, and controllers is typical, these programmable logic devices, processors, or controllers can be combinable in various ways without affecting the functional operation of the imaging device and the application of the invention. These programmable logic devices, processors, or controllers can comprise one or more programmable logic devices, digital signal processor devices, microcontrollers, or other digital logic circuits. Although a combination of such programmable logic devices, processors, or controllers has been described, it should be apparent that one programmable logic device, digital signal processor, microcontroller, or other digital logic circuit can be designated to perform all of the needed functions. All of these variations can perform the same function and fall within the scope of this invention.

Figure 16:
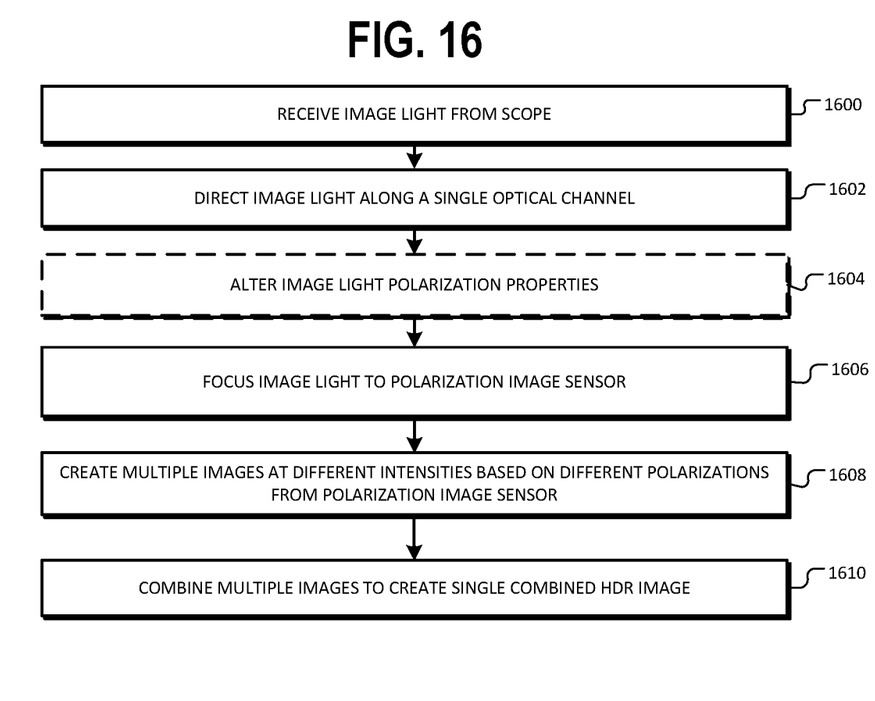
FIG. 16 is a flowchart of a process for producing high dynamic range images according to some embodiments.

FIG. 16 is a flowchart of a method for producing endoscopy images according to an example embodiment. The method may be performed under control of a processor such as system controller 50 (FIG. 15), employing any of the various example embodiments of a camera head or joint endoscope and camera head devices as described herein, with a suitable camera control unit such as that described above to process the image data. Other types of medical scopes or borescopes may be used in place of the endoscope as discussed above. The method begins at process block 1600 where it includes receiving the image light from an endoscope. The endoscope device used may be a separate device attached to a camera head or an endoscope integrated with a camera head. At process block 1602, the process directs the received image light along a single optical channel. At block 1604, the process may alter the polarization properties of the image light with the polarization control element. This may be done in a time varying manner, such as by rotating a rotating polarizer or varying a variable retarder. Block 1604 may include causing the polarizing optical element to change relative intensity detected by the pixels in each subgroup dynamically based on the content of the received image, such as a camera control unit (CCU) determining that portions of a captured first image, second image or combined image is underexposed or overexposed, and adjusting settings as appropriate in the subsequent frame. In some embodiments, the process includes calculating at least one statistical property for the plurality of images (block 1608) such as the intensity value over all pixels or a selected group of representative pixels, and determining which pixels in a certain polarization state have an intensity value below or above a given threshold, and based at least in part on the values of the statistical properties, generate a control signal for the polarizing optical element.

Next at process block 1606 the process includes focusing the first portion of image light on the polarization image sensor. Note that while the steps are depicted in order, typically block 1604 is performed on the light as it is focused toward the sensor, because the focusing lenses are preferably optically positioned ahead of the polarization control elements. At block 1608, the polarization image sensor creates multiple images based on the light at different polarizations as described above.

Next at process block 1610, image processing is performed on the image data from the sensor. The processing is generally applied to image data to generate a single combined image including at least first characteristics resulting from one of the images, and second characteristics resulting from another one of the images. The processing is performed by a CCU such as the CCU 70 of FIG. 14, or other suitable image processing circuitry. Processing the image data with different intensity ranges provides a high dynamic range (HDR) single combined image with higher dynamic range than either the first or second image taken individually. Many suitable HDR algorithms may be used. Known image processing techniques for polarization studies may be applied in processing the multiple images from such an embodiment, permitting, for example, glare reduction in the combined image.

As used herein the terms "comprising," "including," "carrying," "having" "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The foregoing has outlined rather broadly the features and technical advantages of the invention in order that the detailed description of the invention that follows may be better understood. It should be appreciated by those skilled in the art that the conception and specific embodiments disclosed may be readily utilized as a basis for modifying or designing other structures for carrying out the same purposes of the invention. It should also be realized by those skilled in the art that such equivalent constructions do not depart from the scope of the invention as set forth in the appended claims.

Although the invention and its advantages have been described in detail, it should be understood that various changes, substitutions and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

The invention claimed is:

1. An endoscope system comprising:
an endoscope, the endoscope comprising a longitudinal axis, a cover glass, an objective lens group, the objective lens group comprising at least an objective lens, the objective lens group collecting an image light from a subject scene;
a camera system connected to the endoscope, the camera system comprising a first optical group positioned to receive and condition the image light from the endoscope, the first optical group comprising one or more focusing lenses for focusing light onto an image sensor positioned to receive the focused light from the first optical group, the image sensor comprising a plurality of pixels arranged as a plurality of subgroups each subgroup containing at least two pixels, at least one pixel in a respective subgroup having an associated polarizer, whereby a light detected by at least a first pixel of each subgroup is differently polarized than a light detected by a second pixel of a subgroup; and an adjustable polarizing control element with polarizing characteristics positioned distal to the image sensor which, by its polarizing characteristics, is capable of controlling a relative intensity detected by the pixels in each subgroup.

2. The endoscope system of claim 1 further comprising a processor adapted to receive an image data from the image sensor.

3. The endoscope system of claim 2 wherein the processor is further adapted to and generate a high dynamic range (HDR) image from the received image data.

4. The endoscope system of claim 3 wherein the processor is further adapted to create a plurality of images from the received image data and combine the plurality of images in order to generate the HDR image.

5. The endoscope system of claim 1 further comprising connectors between the endoscope and the camera system, the connectors configured such that the endoscope may be detachably connected to the camera system.

6. The endoscope system of claim 1 wherein the endoscope and the camera system are integrated into a single housing.

7. The endoscope system of claim 1 wherein the objective lens group comprises one or more additional lenses.

8. The endoscope system of claim 1 wherein the endoscope is rigid and further comprises one or more rod lenses to pass the image light along the longitudinal axis toward a proximal end of the endoscope.

9. The endoscope system of claim 4 wherein each of the plurality of created images are created from image data received from a set of pixels spanning a plurality of subgroups and having the same respective polarizer orientation.

10. The endoscope system of claim 2 wherein the polarizing optical element changes the relative intensity detected by the pixels in each subgroup dynamically based on the content of the received image.

11. The endoscope system of claim 1 wherein the polarizing optical element is a polarizer capable of rotation, and by its rotation thereby adjusts the relative intensity detected by the various pixels in each subgroup.

12. The endoscope system of claim 1 further comprising a processor adapted to receive an image data from the image sensor, and wherein the polarizing optical element is adjusted dynamically based on the content of the received image data.

13. The endoscope system according to claim 1 wherein the polarizing optical element is a polarizer followed by a variable retarder, and wherein the retardance of the variable retarder may be changed thereby changing the relative intensity detected by the various pixels in each subgroup.

14. The endoscope system of claim 13 further comprising a processor adapted to receive an image data from the image sensor, and wherein the variable retarder is adjusted dynamically based on the content of the received image data.

15. The endoscope system of claim 2, wherein the processor is adapted to calculate one or more statistical properties for the plurality of images and based at least in part on the values of the statistical properties, generate a control signal for the polarizing optical element.

16. The endoscope system of claim 4 wherein the processor is adapted to, when combining the plurality of images to generate a HDR image, select a pixel intensity value for each of the plurality of subgroups based on at least one intensity value from a pixel in the subgroup.

17. The endoscope system of claim 1 wherein the polarizing optical element further comprises beamsplitter, splitting an image beam into a first beam with a first polarization and a second beam with a second polarization, the first beam directed to the image sensor including a plurality of pixels of subgroups, and the second beam directed to a second image sensor.

18. The endoscope system of claim 17 further comprising a second polarizing optical element arranged along an optical path between the beamsplitter and the image sensor including a plurality of pixels of subgroups.

19. The endoscope system of claim 18 wherein the second image sensor also comprises a plurality of pixels arranged as a plurality of subgroups each subgroup containing at least two pixels, at least one pixel in a respective subgroup having an associated polarizer, whereby a light detected by at least a first pixel of each subgroup is differently polarized than a light detected by a second pixel of a subgroup.

20. The endoscope system of claim 18 wherein the second image sensor further comprises a Bayer filter.

* * * * *